United States Patent [19]

Schaumann et al.

[11] Patent Number: 4,889,922

[45] Date of Patent: Dec. 26, 1989

[54] MONOCLONAL ANTIBODY SPECIFIC FOR HUMAN COLON FIBROBLAST-DERIVED T-PA

[75] Inventors: Jon P. Schaumann, Kirkwood; Jitka V. Olander, University City; Nicholaos K. Hrakas, Chesterfield; Joseph Feder, St. Lousi, all of Mo.

[73] Assignee: Monsanto Co., St. Louis, Mo.

[21] Appl. No.: 294,032

[22] Filed: Jan. 6, 1989

Related U.S. Application Data

[62] Division of Ser. No. 896,362, Aug. 13, 1986.

[51] Int. Cl.$^4$ ............... G01N 33/53; G01N 33/544; G01N 3/20

[52] U.S. Cl. ........................ 530/413; 435/7; 435/240.27; 435/212; 436/529; 436/530; 530/357; 530/391

[58] Field of Search ............ 435/7, 212, 240.27; 530/413, 387; 436/529, 530

[56] References Cited

U.S. PATENT DOCUMENTS 4,568,544  2/1986  Hasegawa et al. ............... 424/94
4,751,084  6/1988  Feder et al. ..................... 424/94

FOREIGN PATENT DOCUMENTS 2122219  1/1984  United Kingdom .

OTHER PUBLICATIONS

Einarsson, et al., Biochemica et Biophysica Acta 830 (1985), 1–10.

Reagan, et al., Thromboses Research 40 (1985) 1–9.
Scope, R., Protein Purification–Principles Practice, pp. 121–124, 132–135, Springer-Verlag, N.Y., 1982.
Pettersson et al., Haemostasis 11 (Supp. 1), p. 75, Abst. 134 (1982).
Pettersson et al., Prog. Fibrinolysis 6, 191–194 (1983).
Nielsen et al., The EMBO J. 2(1), 115–119 (1983).
Matsuo et al., Thromb. Res. 36, 517–526 (1984).
MacGregor et al., Thromb. Haemos, 53(1), 45–50 (1985).
Schleef et al., Ibid. 53(1), 170–175 (1985).
Angles-Cano et al., Blood 66(4), 913–920 (1985).
Holvoet et al., Ibid. 67(5), 1482–1487 (1986).
Einarrson et al., biochim. Biophys. Acta 830, 1–10 (1985).
Reagan et al., Thromb. Res. 40, 1–9 (1985).
Tissot and Bachman, Prog. Fibrinolysis 6, 133–135 (1983).
Chemical Abstracts, vol. 105, No. 224438, Dec. 22, 1986.
Chemical Abstracts, vol. 105, No. 224439, Dec. 22, 1986.

Primary Examiner—Christine M. Nucker
Assistant Examiner—Karen I. Krupen
Attorney, Agent, or Firm—Scott J. Meyer; James W. Williams, Jr.

[57] ABSTRACT

A monoclonal antibody is disclosed which is specific for human colon fibroblast-derived tissue plasminogen activator (t-PA), and which is useful for immunoaffinity chromatography purification of t-PA and determination of t-PA in a biological sample.

4 Claims, 3 Drawing Sheets

MONOCLONAL ANTIBODY SPECIFIC FOR HUMAN COLON FIBROBLAST-DERIVED T-PA

This a division of application Ser. No. 06/896,362, filed Aug. 13, 1986.

BACKGROUND OF THE INVENTION

The present invention relates to monoclonal antibodies produced by hybrid cell lines characterized in that the antibodies have specificity to human colon fibroblast-derived tissue plasminogen activator (t-PA). The present invention also relates to the use of the monoclonal antibodies in a method for the purification of t-PA and in a method for the immunoassay of t-PA.

With the advent of hybridoma technology first developed by Köhler and Milstein, it is now possible to generate monoclonal antibodies which are essentially homogenous compositions having uniform affinity for a binding site. The production of mouse hybridomas by these investigators is described in Nature 256, 495–497 (1975); and Eur. J. Immunol. 6, 511–519 (1976). According to this method, tissue-culture adapted mouse myeloma cells are fused to spleen cells from immunized mice to obtain the hybrid cells that produce large amounts of a single antibody molecule. The fusion is generally carried out in the presence of polyethylene glycol (PEG) as described by Galfe et al., Nature 266, 550–552 (1977), followed by selection in HAT medium (hypoxanthine, aminopterin and thymidine) as described by Littlefield, Science 145, 709–710 (1964).

While immunization can be carried out with virtually any foreign antigen of interest, many difficulties arise and variations are required for each specific case. Prior to attempting to prepare a given hybridoma, there is no assurance that the desired hybridoma will be obtained, that it will produce antibody if obtained, or that the antibody so produced will have the desired specificity.

A number of publications have described the preparation of hybridomas that produce monoclonal antibodies against t-PA derived from Bowes melanoma cultured cells, human plasma and human uterine tissue. See, for example, Pettersson et al., Haemostasis 11(Supp. 1), p. 75, abstract 134 (1982); Pettersson et al., Prog. Fibrinolysis 6, 191–194 (1983); Nielsen et al., The EMBO J., 2(1), 115–119 (1983); Matsuo et al., Thromb. Res. 36, 517–526 (1984); MacGregor et al., Thromb. Haemos. 53(1), 45–50 (1985); Schleef et al., Ibid., 53(1), 170–175 (1985); Angles-Cano, Blood 66(4), 913–920(1985); Holvoet et al., Blood 67(5), 1482–1487(1986); and UK Patent Application GB 2,122,219, published Jan. 11, 1984. Such hybridomas have been used to produce monoclonal antibodies which have been used for in vitro purification of Bowes melanoma t-PA as described, for example, by Einarsson et al., Biochim. Biophys. Acta 830, 1–10 (1985); and Reagan et a., Thromb. Res. 40, 1–9 (1985). Several of these monoclonal antibodies against Bowes t-PA are available commercially, e.g. from American Diagnostica Incorporated, Greenwich, Connecticut (ADI).

Recently, in copending application Ser. No. 849,933, filed Apr. 9, 1986, three of the present inventors together with others described a process for preparing human colon fibroblast-derived t-PA. The unique, heterogeneous glycosylation pattern in this t-PA is described in copending application Ser. No. 834,080, filed Feb. 26, 1986, by one of the present inventors together with others, now U.S. Pat. No. 4,751,084. The disclosures of said copending applications which are assigned to a common assignee, are incorporated by reference herein.

Monoclonal antibodies against human colon fibroblast t-PA have not been described heretofore although it has been reported by Tissot and Bachman, Prog. Fibrinolysis 6, 133–135 (1983), that monoclonal antibodies against Bowes melanoma t-PA recognize t-PA from colon tissue

BRIEF DESCRIPTION OF THE INVENTION

In accordance with the present invention novel monoclonal antibodies are provided which are produced by hybrid cell lines characterized in that the antibodies have specificity to human colon fibroblast t-PA. These antibodies are useful in methods for the purification of t-PA and in the immunoassay of t-PA.

The purification of t-PA from a biological sample containing t-PA can be carried out by immunoaffinity chromatography in which the biological sample is passed through an immunoadsorbent column comprising the novel monoclonal antibodies of this invention bound to a solid phase support to thereby selectively adsorb said t-PA.

The immunoassay of t-PA for determining the level of t-PA in a biological sample containing t-PA can be carried out by contacting said sample with a known amount of the novel monoclonal antibodies of this invention and measuring the resulting amount of adsorbed monoclonal antibody.

Three preferred hybrid cell lines for use in making these antibodies are designated as cell lines PA 63-4, PA 54-2 and PA 79-7. They are more conveniently designated hereinafter solely by the stated numbers without the PA prefix. Isolates of these hybrid cell lines are on deposit in the permanent collection of the American Type Culture Collection, Rockville, Maryland, under accession numbers ATCC HB 9155, ATCC HB 9157, and ATCC HB 9156, respectively. Samples of these cell lines can be obtained by the public upon request to that depository as of the date of the grant on a patent disclosing the culture by its accession number.

The human colon fibroblast t-PA against which the antibodies of this invention have specificity can be isolated from the normal human colon fibroblast cell line CCD-18Co. This cell line is on deposit without restriction in the permanent collection of the American Type Culture Collection, Rockville, Maryland, under accession number ATCC CRL-1459. Samples of the cell line can be obtained by the public upon request to that depository.

DETAILED DESCRIPTION OF THE INVENTION

While the specification concludes with claims particularly pointing out and distinctly claiming the subject matter regarded as forming the present invention, it is believed that the invention will be better understood from the following description taken in connection with the accompanying drawings in which:

Figure 1:
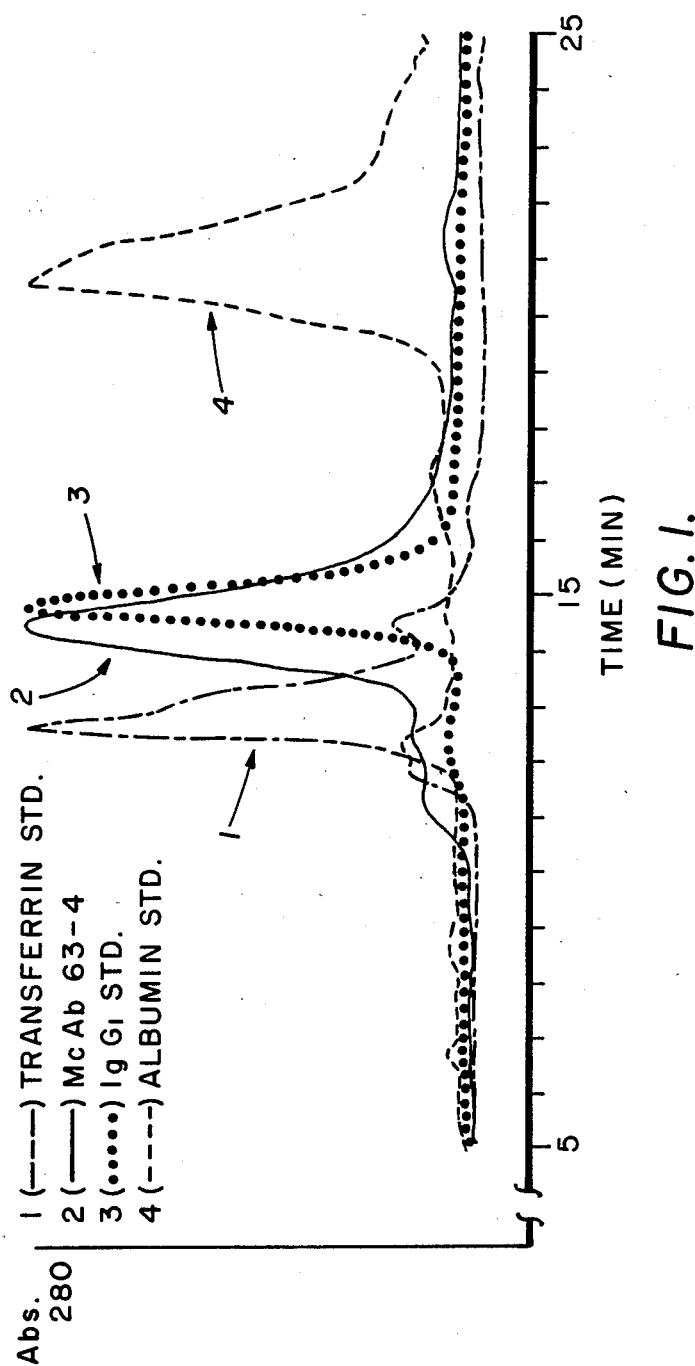
FIG. 1 shows the high performance liquid chromatography (HPLC) profile of monoclonal antibody to human colon fibroblast t-PA purified on a Protein A-Sepharose affinity column and then chromatographed on a Bio-Gel TSK DEAE-5-PW ion exchange HPLC column in one embodiment of the invention.

HYBRIDOMA PREPARATION AND INITIAL CHARACTERIZATION OF MONOCLONAL ANTIBODIES AGAINST HUMAN COLON FIBROBLAST t-PA

The initial t-PA antigen used to immunize mice was obtained from the same batch of material and purified by the same sequence of steps described in Table 1 of Example 2 in the aforesaid copending application Ser. No. 849,933, except that the sample was purified two times (two passes over the TSK 3000 SW Size Exclusion HPLC Column in the final purification step. These steps consisted of subjecting the conditioned medium of the cultured normal human colon fibroblast cells CCD-18Co (ATCC CRL-1459) to a first affinity chromatography with zinc chelate-agarose and then a second affinity chromatography with concanavalin A-agarose followed by TSK 3000 SW size exclusion high performance liquid chromatography. The final t-PA sample had the following characteristics:

Volume = 3 ml (in H$_2$O + 0.01% Tween ® 80);

Protein Concentration = 0.3 $\frac{mg}{ml}$ [as determined by the method of Bradford, Anal. Biochem. 72, 248–254(1976)]

Plasminogen Activator Activity = $\frac{480}{ml}$ Ploug Units (determined by the PA spot assay method of copending application Ser. No. 849,933)

t-PA antigen ≃ 0.15 $\frac{mg}{ml}$ (purity estimated to be 50% by the SDS-PAGE method of copending application Ser. No. 849,933)

Mice Immunization

Three mice (young adult BALB/c, ByJ, female) were immunized subcutaneously as follows: each mouse received 15 μg of the above t-PA antigen in two subcutaneous injections of 0.1 ml each in complete Freund's Adjuvant (water-in-oil emulsion with mycobacteria, Davis et al., *Microbiology*, 3rd Edition, Harper and Row Publishers, New York, NY, 1980, pp. 436–437) in the back and right flank. Two weeks later each mouse received the same injection in different sites on the back and left flank, except in Incomplete Freund's Adjuvant (water-in-oil emulsion without mycobacteria). After two additional weeks each mouse received a final boost intraperitoneally (i.p.) of 50 μg of the t-PA in 0.2 ml phosphate buffered saline (PBS =0.01–0.02 M sodium phosphate, 0.15 M NaCl, pH 6.8-7.4). Three days later the spleens were removed for fusion.

Hybridoma Preparation

Immune spleen cells were fused with Sp2/0 - Ag 14 myeloma fusion partners following essentially the procedure of Davie, Hybridomas: A Revolution in Reagent Production, *Pharmacological Reviews*, 37 (1), 115–118 (1982). The Sp2/0-Ag 14 is a well-known cell line of BALB/c origin defined by Schulman et al., *Nature* 276, 269–270 (1978). These cells which do not synthesize Ig chains are available from the Basel Institute for Immunology and from the American Type Culture Collection under accession number ATCC CRL-1581. Optimal results for fusion required log growth of the Sp2 fusion partner in medium containing 15% Hyclone fetal calf serum. Sp2 cells were passed daily, diluting them to 5×10$^5$ cells/ml, 15 ml total volume in a T-75 flask, for 3 days prior to fusion. After fusion, cells were dispersed into 6, 96-well plates and approximately 60 cells/well of human foreskin fibroblasts were added as feeder cells —all in HAT selection medium containing 15% Hyclone FBS (fetal bovine serum) carefully selected to support new hybrid cell growth. Of 600 wells seeded, 400 (75%) contained growing hybridomas, 150 were screened for production of monoclonal antibodies to t-PA by ELISA (Enzyme-Linked Immunosorbent Assay), and 15 (10%) were positive. The ELISA was carried out essentially by the method of Engvall and Perlmann, *J. Immunol.* 109, 12914 135 (1972). Selected hybridomas were subcloned essentially according to the method of Bishop, *J. Immunological Methods*, 46, 47–51 (1981); Davis et al., *Ibid.*, 50, 161–171 (1982).

Monoclonal Antibodies to Colon t-PA: Initial Characterization

Five of the t-PA positive hybridomas prepared above survived subcloning and these were characterized further as shown in Table I. All the clones were moderate producers of monoclonal antibodies, 10–20 μg/ml (10–20 μg of monoclonal antibody per ml of conditioned medium), with IgG$_1$ isotype; all 5 monoclonal antibodies cross-reacted with Bowes melanoma t-PA but not with urokinase (u-PA).

Three of the monoclonal antibodies were selected to further illustrate the invention and tested for use in t-PA purification and in immunoassay of t-PA. Five hundred milliliters of conditioned media from each of clones 63-4, 54-2 and 79-7 were used to isolate the monoclonal antibodies on Protein A-Sepharose ® columns and then conjugated to cyanogen bromide activated Sepharose to produce immunoabsorbent columns. Partially purified t-PA separated from the conditioned medium of CCD-18Co colon fibroblast cells by affinity chromatography first with zinc chelate-Sepharose 6B and then with concanavalin A-Sepharose 4B, as described in copending application Ser. No. 849,933, was passed over such a column made with the 63-4 monoclonal antibody and eluted with KSCN and the three eluted fractions were analyzed on reduced SDS-PAGE:

1M KSCN fraction—0 t-PA,
2M KSCN fraction—1 and 2 chain t-PA, and
4M KSCN fraction->75% 1 chain t-PA.

The material was judged to be pure by sodium dodecylsulfate polyacrylamide gel electrophoresis (SDS-PAGE) with no detectable urokinase contamination as determined by Western Blot methodology defined hereinafter. This preliminary test indicated that the 63-4 monoclonal antibody binds single-chain t-PA somewhat tighter than the two-chain protein. The three hybridomas (63-4, 54-2 and 79-7) were scaled up to 10 L in order to provide sufficient monoclonal antibodies for further tests.

TEST METHODS FOR EVALUATION OF MONOCLONAL ANTIBODIES

Purification of t-PA Methodology

To evaluate the monoclonal antibodies to human colon fibroblast t-PA as defined herein, comparisons were performed between these antibodies and a commercial preparation of a monoclonal antibody (PAM-1) to Bowes t-PA in the purification of colon t-PA as well as of commercially available Bowes melanoma t-PA [PAM-1 and Bowes t-PA were purchased from American Diagnostica, Inc., Greenwich, CT, (ADI)]. For example, a vial from ADI of PAM-1Sepharose, containing 10 mg IgG per 1.7 ml of gel, was gently stirred with 25 ml of a dialyzed Concanavalin A-Sepharose (Con A) eluate fraction of colon t-PA for 4 hours at room temperature. The Con A t-PA fraction had been prepared essentially as described in copending Application Ser. No. 849,933, in which the conditioned medium of the cultured normal human colon fibroblast cells CCD-18Co were subjected to a first affinity chromatography with zinc chelate agarose and then a second affinity chromatography with Con A. The solution was filtered, washed and poured into a small column. After washing with PBS and 0.25M KSCN, the t-PA was eluted with 1.6 M KSCN. Similar tests were repeated using monoclonal antibodies isolated in accordance with the invention defined herein, by varying column and batch adsorption techniques and elution agents. Tested were variations of the concentration of antibody attached to the Sepharose, of the concentration of KSCN used to elute the t-PA, of the ratio of 1-PA to antibody used in the charge and the effectivity of batch vs. column methods in binding t-PA in conditioned media.

Western Blot Methodology

This methodology followed essentially the method described by Renart and Sandoval, *Meth. Enzymol.* 104(C), 455–460 (1984), modified as follows. One microgram amounts of t-PA and u-PA (apparent mol. wt., $M_r$, 54,000, Calbiochem, LaJolla, Calif.) were subjected to SDS-PAGE. Bowes melanoma t-PA from ADI and human colon fibroblast t-PA purified by immunoaffinity chromatography with the monoclonal antibodies of this invention were thus used. After electrophoresis, the proteins were electroblotted onto activated paper and allowed to react with a 1:3000 dilution of a commercial anti-urokinase (Cat. No. 6200, anti-human urokinase, rabbit serum, Green Cross Corp., Osaka, Japan . The bound antibody was labeled with $^{125}$I-Protein A (New Enqland Nuclear, Boston, Massachusetts). After washing, the radio-labeled immunolabeled paper was exposed to X-ray film. Any detected urokinase was evident as a dark exposed spot on the X-ray film.

Protein A

Protein A immobilized on agarose beads, as supplied by Pharmacia, was used as a matrix for a simple one-step purification procedure for immunoglobulins. Chromatography was performed with the Affi-Gel® Protein A MAPS buffer system supplied commercially in kit form by Bio-Rad Laboratories, RiChmond, California, which essentially involved diluting the conditioned media with the supplied binding buffer, passing the diluted conditioned media over a column of Protein A-Sepharose, washing off the extraneous protein and eluting the bound immunoqlobulin with the supplied elution buffer.

Binding Phenomena

Binding affinity was estimated by an antibody dilution technique essentially as described by Van Heyningen et al., *J. Immunol. Meth.* 62, 147–153 (1983) in which an enzyme-linked immunosorbent assay [ELISA, Engvall and Perlman, *J. Immunol.* 109, 129–135 (1972)] measures the binding of serial dilutions of monoclonal antibody to immobilized t-PA. Fifty microliters ($\mu$l) containing 160 nanograms (ng) of purified t-PA in a washing buffer composed of 0.605 grams tris [tris(hydroxymethyl)aminomethane], 4.05 grams sodium chloride and 1 ml of Tween 20 (Polysorbate 20, Sigma, St. Louis, Missouri) adjusted to pH 8 with HCl and diluted to 500 ml, was added to each well of a 96-well tissue culture grade (wettable) plastic plate. The plates were dried and stored desiccated at room temperature. The wells were washed with the washing buffer immediately before use. After washing and flicking the plates to remove excess buffer, 50 $\mu$l of serial two-fold dilutions of antibody in the above buffer containing b 10 mg/ml bovine serum albumin was added to duplicate wells. The plates were covered and incubated at 37° C. After two hours the plates were washed three times with the washing buffer above and flicked to remove excess liquid. Fifty $\mu$l of a 1:200 dilution of goat anti-mouse immunoglobulin conjugated with alkaline phosphatase in buffer containing bovine serum albumin was added to each well and the pate was again incubated at 37° C. for two hours. The plate was washed three times with serum-free buffer, and then to each well was added 100 $\mu$l of a 1 mg/ml solution of paranitrophenylphosphate in a solution of 48 ml diethanolamine and 0.24 mM magnesium chloride, pH 9.8, diluted to 500 ml with deionized water. Color was allowed to develop for 30 minutes at room temperature and read at 410 nm either rapidly on an automatic plate reader or the reaction was stopped with 50 $\mu$l of 2 M sodium hyroxide for delayed reading. The relative binding parameters thus obtained are shown in Tables VI and VII hereinafter.

The foregoing illustrates the use of the monoclonal antibodies of this invention in an immunoassay for determining the level of t-PA in an ELISA type test. In this test, t-PA is adsorbed to a solid carrier surface such as a plastic plate and the adsorbed t-PA is then reacted with the monoclonal antibody. The amount of adsorbed monoclonal antibody is then measured spectrophotometrically using an enzyme-labeled second antibody. When an appropriate enzyme substrate is added, the optical density of the final solution is directly proportional to the amount of t-PA in the original sample.

In a typical example of the immunoassay method of the invention, the monoclonal antibody to the colon fibroblast t-PA is used to coat plastic wells and capture (bind) the t-PA in samples added to the wells, such as a patient's serum sample having an unknown concentration of t-PA to be determined or standard control solutions of known t-PA concentration. The reaction complex thereby formed in the wells is made to further react with an enzyme-labeled second monoclonal antibody applied to the wells. The amount of the second antibody which binds to the complex is proportional to the concentration of the t-PA in the original sample. The enzyme-labeled antibody can be detected by adding a chromogenic substrate to the wells and measuring the optical density after a predetermined specific reaction time. The concentration of t-PA can then be read from a standard curve generated with each assay.

Electrophoresis

Polyacrylamide gel electrophoreses followed essentially the procedure of Laemmli, *Nature* 227, 680 (1970). Reduced gels were prepared using either mercaptoethanol or dithiothreitol in sodium dodecyl sulfate buffers.

t-PA Quantitation

For routine t-PA screening, either a PA spot assay as described in copending application Ser. No. 849,933 or a direct colorimetric assay in Microtiter plates utilizing S-2322 (D-Val-Gly-Argparanitroanilide) or S-2444 (D-Glu-Gly-Arg-paranitroanilide) (enzyme substrates from Kabi) as described by Wallen et al., *Eur. J. Biochem.* 132, 681–686 (1983) were used. In the PA spot assay, activity is expressed as Ploug units per ml as determined by applying 5 $\mu$l of sample onto the surface of an agarose gel in a petri dish containing fibrinogen, thrombin and plasminogen. The cloudy gel is cleared in an area proportional to the t-PA activity. Both of these assays were standardized against solutions of urokinase or commercial t-PA or a WHO standard t-PA as defined by Gaffney and Curtis, *Thromb. Haemost.* 53 134–140 (1985).

To quantify u-PA in preparations that also contained t-PA, the substrate Chromozym ® PL (Tosyl-glycyl-prolyl-lysine-4-nitranilide acetate), commercially available from Boehringer Mannheim Biochemicals, Indianapolis, Indiana (Cat. No. 378–461), was used together with substrate S-2322 as described by Rijken, *Plasminogen Activator From Human Tissue*, Ph.D. Thesis, University of Leiden, Netherlands, p. 70 (1980).

Radial Immunodiffusion Assays

This assay, developed by Mancini et al., *Immunochem.* 2, 235–254 (1965), is based on the principle that a visible precipitate forms when a soluble antigen and its specific antibody react in the appropriate proportion. In this assay an antibody against IgG$_1$ immunoglobulin is incorporated in an agarose gel and the immunoglobulin to be assayed is placed in a well cut into the gel. As the sample of immunoglobulin diffuses radially outward from the well it reacts with the antibody, forming a visible ring of precipitate. The ring of precipitate continually forms and redissolves at an increasing diameter until all the antigen present in the sample has reacted. At this point, the area of the visible ring is directly related to the quantity of immunoglobulin originally introduced into the well. The ring areas are compared with the ring areas of standard solutions of mouse IgG$_1$ that were processed simultaneously. Actual values were determined from standard curves that were generated either on graph paper or mathematically. Plates and standards obtained commercially from TAGO Inc., Burlingame, California, were used.

FURTHER CHARACTERIZATION OF MONOCLONAL ANTIBODIES AGAINST HUMAN COLON FIBROBLAST t-PA

Purification of Monoclonal Antibodies

Protein A immobilized on Sepharose ® (agarose beads), as supplied by Pharmacia, was used as a matrix for a simple one-step purification of the monoclonal antibodies. As stated above, these monoclonal antibodies had been produced in tissue culture by hybridomas selected for their desired properties. Purification by chromatography was performed with the Affi-Gel Protein A MAPS buffer kit supplied by Bio-Rad (Cat. No. 153-6160, Bio-Rad, Richmond, California). The tissue culture media into which the hybridomas had secreted the monoclonal antibodies was diluted with an equal volume of the supplied binding buffer (Bio-Rad) and washed over the Protein A-Sepharose affinity column. Immunoglobulins, including the monoclonal antibody of interest, are bound to the Protein A-Sepharose. Other proteins and unwanted chemicals are washed from the monoclonal antibodies bound to the column with about 15 column volumes of the binding buffer and eluted with the supplied elution buffer (Bio-Rad). This purification was monitored by measuring the UV absorbance of the various fractions, quantitating the protein by Coomassie protein [Bradford, *Anal. Biochemistry*, 72:248–254 (1976)]analysis and radial immunodiffusion (TAGO, Inc., Burlingame, CA, Cat. No. 1346) by the method of Mancini, *Immunochemistry*, 2:235–254 (1965) to quantitate mouse IgG$_1$, and checking the purity by agarose gel electrophoresis and HPLC as shown in FIG. 1.

In FIG. 1, 50 $\mu$l (119 $\mu$g/ml Coomassie Protein) of monoclonal antibody 63-4 that had been purified on a Protein A-Sepharose affinity column was chromatographed on a Bio-Gel TSK DEAE-5-PW (Bio-Rad, Richmond, California) ion exchange HPLC column with a buffer of 0.02 M Tris-HCl, pH 8.5, and eluted with a gradient increasing to 0.02 M Tris-HCl, pH 7.0, 0.3 M NaCl at 1 ml/min. Samples of commercial bovine albumin, bovine transferrin and mouse IgG$_1$ were chromatographed under identical conditions to serve as standards (all obtained from Sigma, St. Louis, Missouri). The plots of time vs. absorbance of 280 nm were overlaid and the absorbance scale was normalized for comparison purposes. Table 11 indicates the relative purification obtained using these procedures. Twenty cubic centimeters of Protein A-Sepharose was used for each of these purifications of the monoclonal antibodies of interest. The chromatography was performed at 4° C.

Immobilization of Monoclonal Antibodies

The immobilization to a Sepharose ® matrix of each of the monoclonal antibodies was carried out according to the following procedure.

1. About 600 mg of freeze-dried Pharmacia CNBr-activated Sepharose 4B was swollen for at least 15 minutes in 1 mM HCl and washed with 120 ml of 1 mM HCl on a sintered glass filter to remove preservatives and stabilizers that may have been added to the product.
2. 2.7 mg of Protein A affinity purified monoclonal antibody (of clones 63-4, 54-2 and 79-7) in phosphatebuffered saline (PBS) was diluted to 4 ml with 0.1 M NaHCO$_3$ buffer, pH 8.3.
3. The gel was washed with about 5 ml of the NaHCO$_3$ buffer and immediately mixed with the diluted monoclonal antibody and mixed gently by tumbling overnight in the cold room at 4° C.
4. The gel was filtered and transferred to 20–40 ml of 1 M ethanolamine, pH 8, for 2 hours at room temperature to block any remaining active sites on the gel.
5. The gel was washed with 0.1 M sodium acetate buffer containing 0.5 M NaCl, pH 4.

6. The gel was again washed with the NaHCO3 buffer and finally equilibrated with PBS.
7. A small Polystyrene column (8 mm. I.D., from Pierce Chemical, Rockford, Illinois, Cat. No. 29920) was used to hold the monoclonal antibody affinity column to eliminate any undersired hydrophobic binding of t-PA to glass.

Purification of t-PA—Detailed Procedure

Figure 2:
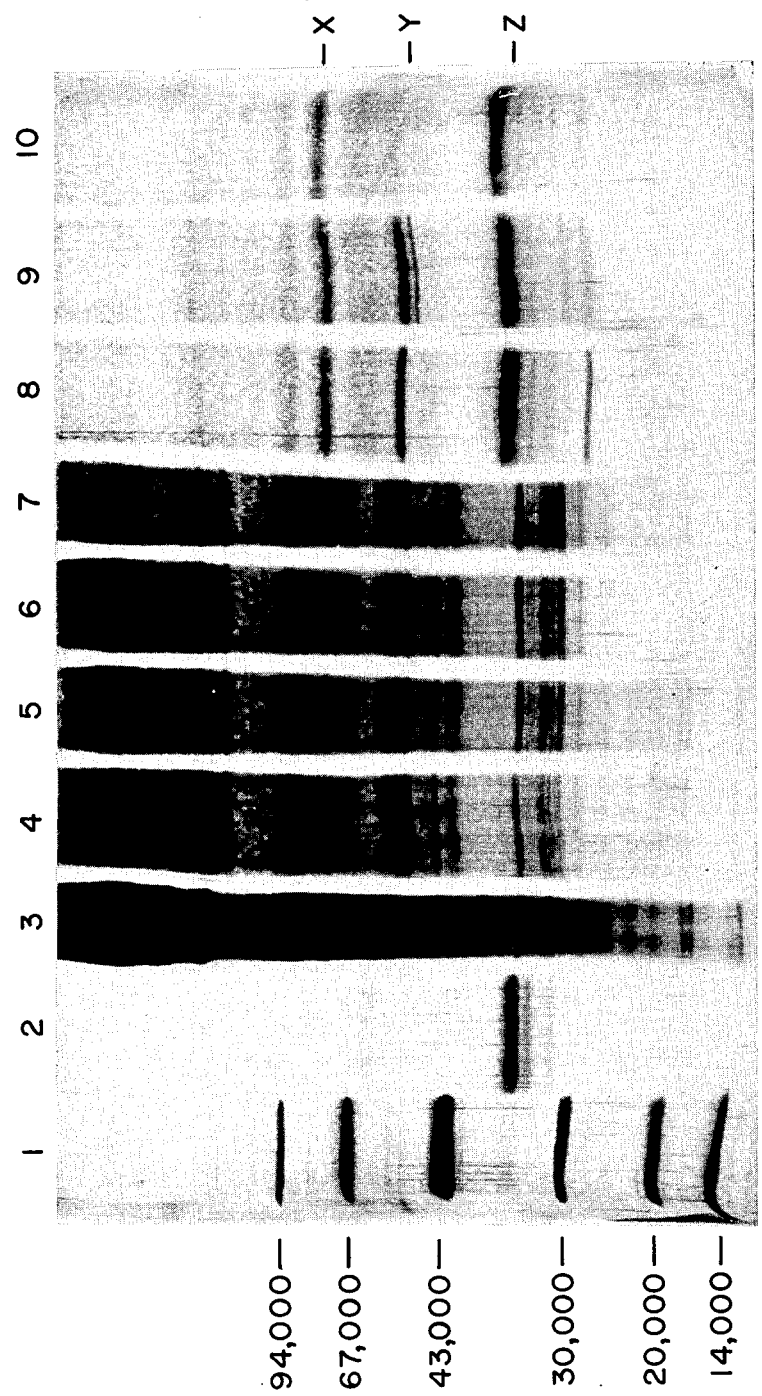
FIG. 2 shows the reduced sodium dodecylsulfate polyacrylamide gel electrophoresis (SDS-PAGE) patterns of human colon fibroblast t-PA purified by immunoaffinity chromatography with monoclonal antibody to human colon fibroblast t-PA immobilized on Sepharose 4B by CNBr in three other embodiments of the invention (lanes 8, 9 and 10).
Figure 3:
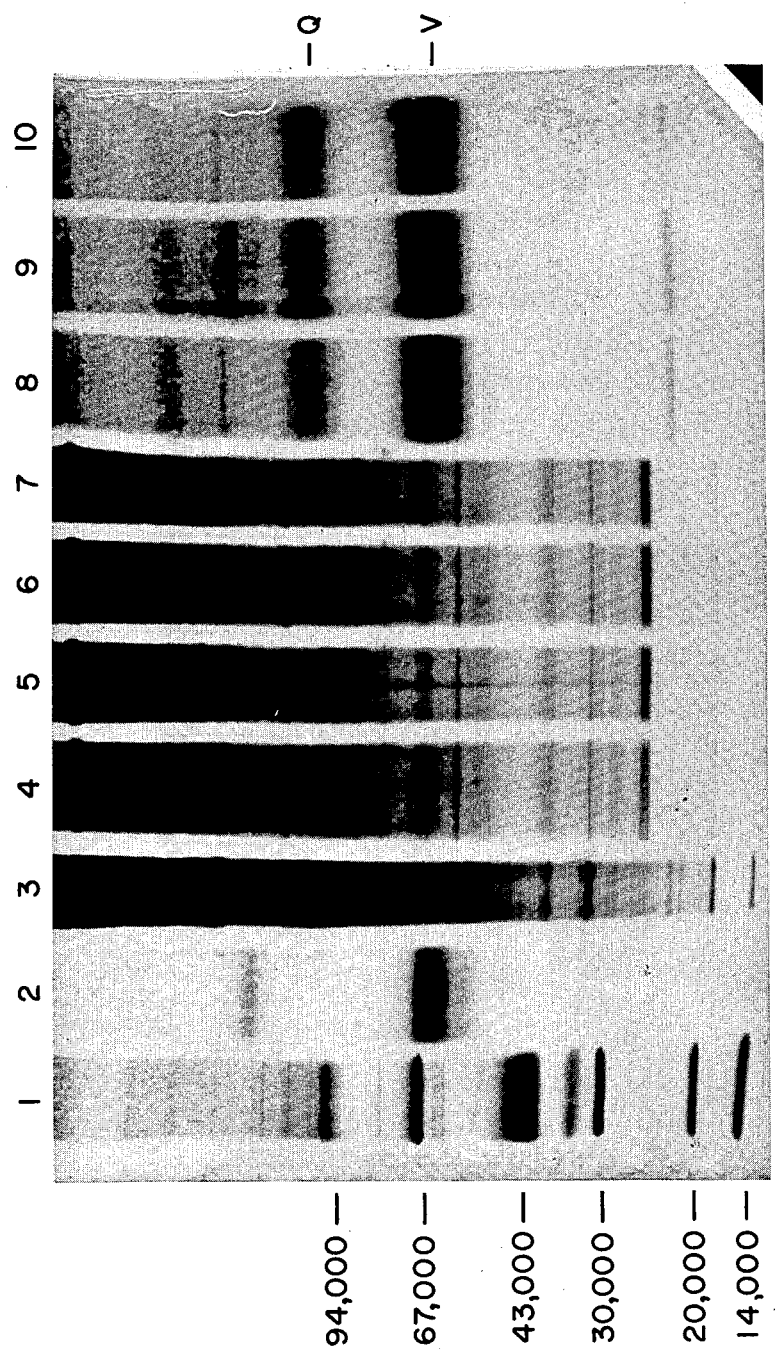
FIG. 3 shows the non-reduced SDS-PAGE patterns of the three monoclonal antibody embodiments of FIG. 2.

An estimate of urokinase contamination of colon fibroblast t-PA preparations was made by examination of a sample of t-PA that had been purified by affinity chromatography using zinc chelate-Sepharose 6B followed by concanavalin A-Sepharose. The direct colorimetric assay method using substrates S-2322 and Chromozym PL were used to estimate the molar concentrations of the two plasminogen activators. In this sample, 1.7% of the total plasminogen activator concentration was urokinase. It was desired to determine if use of the monoclonal antibody against colon fibroblast t-PA immobilized on a solid support matrix such as Sepharose could be used to (a) completely remove u-PA activity, and (b) purify colon fibroblast t-PA or other t-PA to homogeneity. Therefore, a monoclonal antibody column constructed from the 63-4 monoclonal antibody attached to cyanogen bromide activated Sepharose was used to further purify the sample. The urokinase activity remained in solution and passed through the column. 2 M and 4 M KSCN were used to elute some of the t-PA activity from the column (Table III). The eluted fraction was tested for the presence of u-PA by the Western Blot Method and none was detected. Thus, a major objective in purification was achieved. The recovery of t-PA in this run was low because mechanical problems were encountered. In subsequent tests more than 90% of the t-PA activity (as measured by ELISA) from the monoclonal antibody affinity columns was recovered as is shown in Table IV using three different monoclonal antibodies. Thus, a second major objective was achieved whereby t-PA could be purified to homogeneity. SDS-PAGE of the starting material and purified fractions was used to demonstrate the purification capability of the immunoaffinity chromatography method of the invention. FIGS. 2 and 3 show the electrophoretic pattern of the eluted t-PA from the monoclonal antibody column with a linear gradient of KSCN.

In FIGS. 2 and 3, lanes 1 to 10 are as follows:

Lane 1 —Pharmacia low molecular weight standards: $M_r$ 94,000, Phosphorylase B, 0.64 μg; $M_r$ 67,000, Bovine Serum Albumin, 0.83 μg; $M_r$ 43,000, Ovalbumin, 1.47 μg; $M_r$ 30,000, Carbonic Anhydrase, 0.83 μg; $M_r$ 20,000, Soybean Trypsin Inhibitor, 0.8 μg; $M_r$ 14,000, αLactalbumin, 1.21 μg.

Lane 2 —ADI Bowes t-PA, 3 μg.

Lane 3 —Con A fraction of colon t-PA, 0.5 μg.

Lane 4 —Con A fraction of lane 3 dialyzed against water, 0.5 μg.

Lanes 5, 6 and 7 —Unbound fractions from monoclonal antibodies 63-4, 54-2 and 79-7, respectively, 3 μg each.

Lanes 8, 9 and 10 —Eluate from monoclonal antibodies of lanes 5, 6 and 7, respectively, with 4 M KSCN, 2 μg each.

The SDS-PAGE was silver stained by the method of Morrissey, *Anal. Biochem.* 117, 307–310 (1981).

The reduced SDS-PAGE of t-PA purified on three different monoclonal antibodies are similar except for one difference. Common to all of the samples in FIG. 2 are two major bands (Z and X) in lanes 8, 9 and 10 corresponding to apparent molecular weights ($M_r$) of about 36 kilodaltons (Kd) and 69 Kd. The lower molecular weight band (Z) contains the A and B chains of plasmin cleaved t-PA such as described by Bachmann and Kruithof, *Seminars in Thrombosis and Hemostasis* 10(1), 6–17 (1984). The band (X) at 69 Kd corresponds to uncleaved single-chain t-PA. A third band (Y) at 49 Kd, which does not appear in the t-PA purified on PA 79-7 (lane 10), may be free t-PA fragments or an immunologically recognized protein.

The non-reduced SDS-PAGE of the purified t-PA is shown in FIG. 3 in a band (V) at a molecular weight, $M_r$, of about 67,000 and a minor band (Q) at a $M_r$ of about 98,000, which may be a complex of t-PA with some contaminating proteins. The t-PA thus purified (band V) with the three monoclonal antibody matrices 64-3, 54-2 and 79-7 (in lanes 8, 9 and 10, respectively), can be further purified to homogeneity using size exclusion HPLC such as that described in copending application Ser. No. 849,933. The effective reuse of the 79-7 immunoaffinity matrix column is demonstrated by the results shown in Table V as indicated by the similar fold purification in both runs. Substantially similar results were obtained by purification of t-PA derived from other sources.

Binding affinity was estimated by the method described above for monoclonal antibody 63-4 for colon t-PA and compared against Bowes melanoma t-PA obtained commercially from ADI. The results are shown in Table VI. The estimate of binding affinity for PAM-3 monoclonal antibody against Bowes t-PA agrees with the value published by ADI for that system in its technical brochure ADI 84-08-08. Similarly, the relative binding affinity of the three monoclonal antibodies 63-4, 54-2 and 79-7 was compared against the PAM-3 monoclonal antibody as shown in Table VII.

The following is a brief summary of the data shown in detail in Tables I to VII:

Table I describes the characteristics and specificity of a number of antibodies derived from the five listed hybridomas.

Table II provides a step-wise description of the purification of the three listed monoclonal antibodies. It indicates the course of the monoclonal antibody and other protein during the purification steps.

Table III shows that a relatively complete separation of t-PA and urokinase can be aChieved by immunoaffinity with the listed monoclonal antibody. The urokinase passes through the column but the t-PA is retained. The t-PA is later eluted from the column without any detectable urokinase.

Table IV provides a step-wise description of the purification of t-PA on columns of the three listed monoclonal antibodies immobilized on a solid support.

Table V describes a second batch of t-PA purified on the same column described in Table IV. It is intended to show that the column made from monoclonal antibody 79-7 can be reused.

Table VI indicates the binding affinity of monoclonal antibody 63-4 compared with commercial PAM-3 for colon and Bowes t-PA. The binding constant for PAM-3 vs. Bowes t-PA as published by ADI agrees with the binding affinity determined herein.

Table VII provides a comparison of the relative binding of the listed monoclonal antibodies for colon and Bowes t-PA which infers that the different binding characteristics indicate different potential uses.

TABLE I

Characteristics of Monoclonal Antibodies to Colon t-PA

| Hybridoma | Sub-class | Ab[a] (μg/ml) | ADI[b] t-PA | Urokinase[c] | Colon t-PA A[d] | Colon t-PA B[d] |
|---|---|---|---|---|---|---|
| 29-2 | IgG$_1$ | 10-20 | + | − | + | + |
| 54-2 | " | " | + | − | + | + |
| 63-4 | " | " | + | − | + | + |
| 79-7 | " | " | + | − | + | + |
| 86-2 | " | " | + | − | + | + |

[a]Measured by ELISA using an IgG$_{2a}$ myeloma standard obtained commercially from Litton-Bionetics, Charleston, S.C.
[b]American Diagnostica, Inc.; Bowes 2-chain t-PA.
[c]Calbiochem urokinase.
[d]Purified t-PA from two different batches of conditioned media of colon fibroblast cells. Each t-PA sample (A and B) was purified by the same sequence of steps described in Table I of Example 2 in copending application Ser. No. 849,933.
+ = positive, i.e., cross reacts with t-PA.
− = negative, i.e., does not cross react with u-PA.

TABLE III

Purification of t-PA on Monoclonal Antibody 63-4

Starting Material = 8.15 nmol t-PA
 = 0.14 nmol u-PA = 1.7% of the total moles of PA activity (moles of u-PA per total moles of u-PA + t-PA)
Unbound Fraction = 0.21 nmol t-PA = 2.5% of charge
 = 0.14 nmol u-PA
2 M KSCN Eluted Fraction = 0.67 nmol t-PA; no u-PA detected
4 M KSCN Eluted Fraction = 0.57 nmol t-PA; no u-PA detected
Total Eluted Fraction = 1.24 nmol t-PA; no u-PA detected

TABLE II

Protein A Purification of Monoclonal Antibodies Against Human Colon Fibroblast t-PA (63-4, 54-2, 79-7)

| Fraction | Volume ml | Micrograms[a] of IgG$_1$ per ml | Milligrams (mg) of Coomassie Protein per ml | Total micrograms of IgG$_1$ | Total mg of Coomassie Protein | % of Total Coomassie Protein |
|---|---|---|---|---|---|---|
| 63-4 | | | | | | |
| St Mat'l | 385 | 144.1 | 8.309 | 55,478.5 | 3,198.97 | |
| Unbound Fraction | 385 | 0 | 8.541 | 0 | 3,288.29 | 87.9 |
| Column Wash | 295 | 0 | 1.429 | 0 | 421.55 | 11.2 |
| Eluted Pre-Peak Fraction | 48 | 0 | 0.040 | 0 | 1.92 | 0.0 |
| Eluted Peak Fraction | 100 | 677.4 | 0.264 | 67,740.0 | 26.4 | 0.7 |
| Eluted Tail Fraction | 160 | 0 | 0 | 0 | 0 | 0 |
| TOTAL | 988 | | | 67,740.0 | 3,738.17 | |
| % ST MAT'L | | | | 122.1 | 116.8 | |
| 54-2 | | | | | | |
| St Mat'l | 1,000 | 10.9 | 4.453 | 10,900 | 4,453 | |
| Unbound Fraction | 1,980 | 0.0 | 1.775 | 0 | 3,514.5 | 99.5 |
| Eluted Peak Fraction | 120 | 85.6 | 0.126 | 10,272 | 15.12 | 0.42 |
| TOTAL | 2,100 | | | 10,272 | 3,529.62 | |
| % ST MAT'L | | | | 94.2 | 79.2 | |
| 79-7 | | | | | | |
| St Mat'l | 1,000 | 30.0 | 4.151 | 30,000 | 4,151 | |
| Unbound Fraction | 2,000 | 0 | 2.101 | 0 | 4,202 | 92.5 |
| Column Wash Fraction | 780 | 0 | 0.408 | 0 | 318.24 | 7.012 |
| Eluted Peak Fraction | 85 | 295.6 | 0.208 | 25,126 | 17.68 | 0.389 |
| Total | 2,865 | | | 25,126 | 4,537.92 | |
| % ST MAT'L | | | | 83.7 | 109.3 | |

[a]Determined by Radial Immunodiffusion
ST MAT'L = Starting Material

TABLE IV

Monoclonal Antibody Purification of Colon t-PA

| Fraction | Volume ml | PU/ml[a] | Protein mg/ml | Total PU | Total Protein mg | Total Recovered, % PU | Total Recovered, % Protein | Specific Activity PU/mg | Purification Factor |
|---|---|---|---|---|---|---|---|---|---|
| St. Mat'l | 150.0 | 95.2 | 0.287 | 14,280 | 43.05 | | | 331.7 | — |
| 63-4 | | | | | | | | | |
| Unbound Fraction | 150.0 | 89.6 | 0.244 | 13,440 | 36.60 | 91.8 | 96.3 | 367.2 | 1.2 |
| Column wash[b] | 50.0 | 8.1 | 0.015 | 405 | 0.75 | 2.8 | 2.0 | 540.0 | 1.6 |
| Column KSCN[c] wash | 10.0 | 2.6 | 0.000 | 26 | 0.00 | 0.2 | 0.0 | | |

TABLE IV-continued
Monoclonal Antibody Purification of Colon t-PA

| Fraction | Volume ml | PU/ml[a] | Protein mg/ml | Total PU | Total Protein mg | Total Recovered, % PU | Total Recovered, % Protein | Specific Activity PU/mg | Purification Factor |
|---|---|---|---|---|---|---|---|---|---|
| Eluate 54-2 | 17.5 | 43.8 | 0.037 | 767 | 0.65 | 5.2 | 1.7 | 1,183.8 | 3.6 |
| Unbound Fraction | 150.0 | 71.4 | 0.215 | 10,710 | 32.25 | 90.6 | 95.5 | 332.1 | 1.0 |
| Column wash[b] | 50.0 | 6.7 | 0.017 | 335 | 0.85 | 2.8 | 2.5 | 394.1 | 1.2 |
| Column KSCN[c] wash | 7.5 | 3.2 | 0.000 | 24 | 0.00 | 0.2 | 0.0 | | |
| Eluate 79-7 | 19.0 | 39.4 | 0.035 | 749 | 0.67 | 6.3 | 2.0 | 1,125.7 | 3.4 |
| Unbound Fraction | 150.0 | 92.4 | 0.253 | 13,860 | 37.95 | 93.7 | 97.2 | 365.2 | 1.1 |
| Column wash[b] | 50.0 | 4.8 | 0.011 | 240 | 0.55 | 1.6 | 1.4 | 436.4 | 1.3 |
| Column KSCN[c] wash | 10.0 | 1.5 | 0.000 | 15 | 0.00 | 0.1 | 0.0 | | |
| Eluate | 17.5 | 38.5 | 0.032 | 674 | 0.56 | 4.6 | 1.4 | 1,203.1 | 3.6 |

[a] u-PA standard - Ploug Units/ml
[b] 0.1 M NaCl + 0.05 M potassium phosphate, pH 7.3
[c] 0.25 M KSCN

TABLE V
Reuse of Monoclonal Antibody (79-7) for Purification of Colon t-PA

| Fraction | Volume ml | PA[a] IU/ml | Protein mg/ml | Total PA[a] IU | % IU Recovered | Total Protein mg | % Protein Recovered | Specific Activity IU/mg | Purification Factor |
|---|---|---|---|---|---|---|---|---|---|
| St. Mat'l | 400 | 15,600 | 0.220 | $6.24 \times 10^6$ | | 88 | | 70,909 | — |
| Unbound fraction | 400 | 17,600 | 0.220 | $(7.04 \times 10^6)$[b] | 96.75 | 88 | 98.423 | 80,000 | 1.1 |
| Column Wash[c] | 20 | 1,100 | 0.025 | $(22,000)$[b] | 0.302 | 0.5 | 0.56 | 4,000 | 0.062 |
| Column PBS Wash | 20 | 145 | 0 | $(2,900)$[b] | 0.040 | | | — | — |
| Column KSCN Wash[d] | 20 | 163 | 0 | 3,260 | 0.045 | | | — | — |
| Eluate | 70 | 2,975 | 0.013 | 208,250 | 2.86 | 0.91 | 1.02 | 228,846 | 3.2 |
| TOTAL | 530 | | | $7.28 \times 10^6$ | | 89.41 | | | |
| % ST MAT'L | | | | 116.6 | 99.997 | | 100.003 | | |

[a] WHO t-PA Standard
[b] u-PA Activity
[c] 0.1 M NaCl + 0.05 M potassium phosphate, pH 7.3
[d] 0.25 M KSCN

TABLE VI

| | Comparison of the Estimated Binding Affinity[a] | |
|---|---|---|
| Monoclonal Antibody Type | Cell Type t-PA | |
| | Colon t-PA | Bowes t-PA |
| 63-4 (colon) | $1\text{-}10 \times 10^8$ | $10^9$ |
| PAM-3 (Bowes) | $1\text{-}10 \times 10^6$ | $1\text{-}10 \times 10^8$ |

[a] Estimated from data obtained by the method of Van Heyningen et al. J. Immunological Methods, 62: 147–153 (1983).

TABLE VII

| | Relative Binding[a] | | | |
|---|---|---|---|---|
| Monoclonal Antibody Type | PAM-3 | 63-4 | 54-2 | 79-7 |
| Colon t-PA | 10 | 10 | 10 | 1 |
| Bowes t-PA | 100 | 10 | 10 | 100 |

[a] Determined by the Method of Van Heyningen et al J. Immunol. Meth. 62, 142–153 (1983).

Various other examples will be apparent to the person skilled in the art after reading the foregoing specification without departing from the spirit and scope of the invention. It is intended that all such other examples be included within the scope of the appended claims.

What is claimed is:

1. An immunoaffinity chromatography method for purifying t-PA from a biological sample containing t-PA comprising passing said sample through an immunoadsorbent column comprising a monoclonal antibody against human colon fibroblast-derived tissue plasminogen activator and produced by a hybridoma having the characteristics of cell lines 63-4 (ATCC HB 9155), 54-2 (ATCC HB 9157) or 79-7 (ATCC HB 9156) bound to a solid support to thereby selectively adsorb said t-PA.

2. The method of claim 1 in which the t-PA in said biological sample is human colon fibroblast-derived t-PA.

3. The minute of claim 1 in which the adsorbed t-PA is eluted from said solid phase support with KSCN.

4. The method of claim 1 in which the solid phase support is agarose.

* * * * *

UNITED STATES PATENT AND TRADEMARK OFFICE
CERTIFICATE OF CORRECTION

PATENT NO. : 4,889,922

DATED : December 26, 1989

INVENTOR(S) : JON P. SCHAUMANN, JITKA V. OLANDER, NICHOLAOS K. HARAKAS and JOSEPH FEDER It is certified that error appears in the above-identified patent and that said Letters Patent is hereby corrected as shown below:

On the title page, the inventor "Hrakas" should read --Harakas--. In col. 4, line 24, "12914 135 should read --129-135--. In col. 5, line 14, "PAM-1Sepharose" should read --PAM-1-Sepharose--. In col. 6, line 23, delete "b". In col. 7, line 15, "Argparanitroanilide" should read --Arg-paranitroanilide--. In Claim 3, line 1, "minute" should read --method--.

Signed and Sealed this

Ninth Day of April, 1991

Attest:

HARRY F. MANBECK, JR.

Attesting Officer

Commissioner of Patents and Trademarks